US00PP37540P2

(12) United States Plant Patent
Gardner

(10) Patent No.: US PP37,540 P2
(45) Date of Patent: Jul. 28, 2026

(54) PEACH TREE NAMED 'Sauzee Treat'

(50) Latin Name: *Prunus persica*
Varietal Denomination: Sauzee Treat

(71) Applicant: Lacey Marie Gardner, Modesto, CA (US)

(72) Inventor: Lacey Marie Gardner, Modesto, CA (US)

( * ) Notice: Subject to any disclaimer, the term of this patent is extended or adjusted under 35 U.S.C. 154(b) by 0 days.

(21) Appl. No.: 18/831,846

(22) Filed: Oct. 6, 2025

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
CPC ..... A01H 6/7463; A01H 5/08
See application file for complete search history.

*Primary Examiner* — Keith O. Robinson

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of large size fruit.
3. Peento shaped, clingstone fruit with firm, white flesh.
4. Fruit with good flavor and eating quality.
5. Fruit with a high degree of attractive lite red skin color.

1 Drawing Sheet

Botanical designation: *Prunus persica.*
Variety denomination: 'Sauzee Treat'.

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, California.

Prior varieties: Among the existing varieties of peach trees, which are known to us, and mentioned herein, 'Sauzee Lady' Peach (U.S. Plant Pat. No. 22,404) and our proprietary non-patented peach seedling selections '342BF522', '180BA183' and '6LR620'.

Origin of the variety: The new and distinct variety of peach tree (*Prunus persica*) was developed by us in our experimental orchard located near Modesto, California as an open pollinated seedling selection from seed of our proprietary non-patented peach seedling selection with the field identification number '342BF522'. The proprietary non-patented peach seed parent (342BF522) originated from a first generation cross between our proprietary non-patented peach seedling selections '180BA183' and '6LR620'. A large number of these open pollinated seedling selections were planted and grown on their own root system. Under close and careful observation, we recognized the desirable tree and fruit characteristics of the present seedling and selected it in 2018 for additional asexual propagation and commercialization.

Asexual reproduction of the variety: In 2018 asexual reproduction of the new and distinct variety of peach tree was by budding to 'Nemaguard' Rootstock (non-patented), as performed by us in our experimental orchard located near Modesto, California, and shows that reproductions run true to the original tree and all characteristics of the tree and its fruit are established and transmitted through succeeding 26 asexual propagations.

SUMMARY OF THE NEW VARIETY

The present new and distinct variety of peach tree (*Prunus persica*) is of large size, vigorous, upright growth and a regular and productive bearer of large size, white flesh, clingstone fruit with good flavor and eating quality. The fruit is further characterized by its peento shape, firm flesh and attractive lite red skin color. In comparison to its proprietary non-patented peach seed parent '342BF522' the fruit of the new variety is 17 days earlier in maturity. In comparison to the commercial variety 'Sauzee Lady' Peach (U.S. Plant Pat. No. 22,404) the fruit of the new variety is approximately 11 days earlier in maturity and is larger in size.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 6 year old specimens grown near Modesto, California, with color in accordance with Munsell Book of Color published in 1958.

Tree:

*Size.*—Large, usually pruned to 3 to 3.5 meters in height and width for economical harvesting of fruit. Size varies with different cultural practices.

*Vigor.*—Vigorous, growth of 1.5 to 2 meters the first growing season. Varies slightly with type and fertility of soil, climatic conditions and cultural practices.

*Form.*—Upright, usually pruned to vase shape.

*Branching Habit.*—Upright, crotch angle approximately 25°, increases with heavy crop load.

*Productivity.*—Productive, thinning and spacing of fruit necessary for desired market size fruit. Number of fruit set varies with climatic conditions during blooming period. Trees often set several times the number of fruits needed for a full crop load.

*Bearer.*—Regular, has had adequate fruit set 5 consecutive years. No alternate bearing observed.

*Fertility.*—Self-fertile.

*Density.*—Medium dense, usually pruned to vase shape to increase air movement and sunlight to enhance fruit color and health of fruit wood.

*Hardiness.*—Hardy in all stone fruit growing areas of California. Tree grown in USDA Hardiness Zone 9. Winter chilling requirement approximately 600 hours at or below 45° F.

Trunk:

*Size.*—Medium, average circumference 25.4 cm at 22.9 cm above ground on a 6 year old tree.

*Stocky.*—Medium stocky.

*Texture.*—Medium shaggy, roughness increases with age.

*Color.*—Varies from 2.5Y 5/4 to 2.5Y 3/2.

Branches:

*Size.*—Medium. Average circumference 11.9 cm at 1.2 meters above ground. Crotch angle approximately 25°, increases with heavy crop load.

*Surface Texture.*—New growth relatively smooth. Mature growth medium rough, roughness increases with age.

*Lenticels.—l Average number* 46 in a 25.8 sq cm area. Average length 3.8 mm. Average width 1.9 mm. Color 7.5YR 4/6 to 7.5YR 3/6.

*Color.*—New growth varies from 5GY 6/6 to 7.5R 4/8. Mature growth varies from 2.5YR 3/4 to 5YR 3/4, varies with age of growth.

Leaves:

*Size.*—Large. Average length 140.1 mm. Average width 36.8 mm.

*Form.*—Lanceolate.

*Apex.*—Acuminate.

*Base.*—Cuneate.

*Margin.*—Serrate.

*Thickness.*—Medium.

*Surface Texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Average length 12.4 mm. Average width 1.3 mm. Longitudinally grooved. Surface-glabrous. Color varies from 2.5GY 6/6 to 5GY 5/6.

*Glands.*—Type-reniform. Size-medium. Average length 1.4 mm. Average diameter 0.8 mm. Number varies from 2 to 4, average number 3. Located primarily on base of leaf blade and upper portion of petiole. Color varies from 2.5GY 5/6 to 5GY 6/6.

*Stipules.*—None present at time of measurement.

*Color.*—Upper surface varies from 5GY 4/8 to 7.5GY 4/6. Lower surface varies from 7.5GY 5/6 to 5GY 5/6. Midvein color 5GY 6/4 to 5GY 5/4.

Flower buds:

*Size.*—Large. Average length 19.3 mm. Average diameter 10.1 mm.

*Hardiness.*—Hardy with respect to California winters.

*Density.*—Medium dense.

*Form.*—Conical, becoming elongated just before opening.

*Pedicel.*—Average length 5.2 mm. Average width 1.2 mm. Surface-glabrous. Color varies from 5GY 6/6 to 5R 3/4.

*Color.*—Varies from 5RP 7/6 to 2.5RP 8/4.

Flowers:

*Blooming Period.*—Date of First Bloom Mar. 8, 2024. Date of Petal Fall Mar. 18, 2024, varies slightly with climatic conditions.

*Size.*—Large. Average height 21.6 mm. Average diameter 23.5 mm.

*Type.*—Rosette.

*Petals.*—Number-normally five, alternately arranged to sepals. Size-large. Average length 20.0 mm. Average width 15.6 mm. Petal apex-rounded. Petal base-truncate. Form-orbicular. Arrangement-overlapping. Margin-sinuate. Color varies from 2.5RP 8/6 to 2.5RP 7/8, fades with age of flower. Both upper and lower surfaces glabrous.

*Sepals.*—Number-normally five, alternately arranged to petals. Sepal apex-rounded. Size-large. Average length 7.0 mm. Average width 4.5 mm. Shape-ovate. Margin-entire. Color-upper surface varies from 2.5GY 5/4 to 7.5R 3/4. Lower surface varies from 5R 3/8 to 7.5R 3/4. Surface-upper surface glabrous, lower surface pubescent.

*Stamens.*—Average number per flower 34. On average, the stamens are below the height of the petals. Filament-average length 14.3 mm. Filament color varies from N 9.5/(white) to 5RP 4/8. Anther color varies from 5R 3/8 to 5Y 8/6.

*Pollen.*—Present, self-fertile. Color varies from 2.5Y 7/10to 5Y 7/10. Production-abundant.

*Pistil.*—Number-normally one. Average length 12.1 mm. Position of stigma an average of 2.9 mm below anthers. Surface-pubescent. Color varies from 10Y 7/6 to 10Y 8/6. Ovary-pubescent.

*Fragrance.*—Moderate, floral fragrance.

*Color.*—Varies from 5RP 7/6 to 7.5RP 7/6.

*Pedicel.*—Average length 5.0 mm. Average width 1.2 mm. Color varies from 2.5GY 7/6 to 5R 3/4. Surface-glabrous.

*Number Flowers per Flower Bud.*—One.

Fruit:

*Maturity When Described.*—Firm ripe and read for consumption.

*Date of First Picking.*—Jul. 22, 2024.

*Date of Last Picking.*—Aug. 1, 2024, varies slightly with climatic conditions.

*Size.*—Large. Average diameter axially 51.2 mm. Average transversely in suture plane 84.5 mm. Average weight 207.3 grams.

*Form.*—Peento shape.

*Suture.*—Lipped.

*Ventral Surface.*—Lipped.

*Apex.*—Retuse.

*Base.*—Retuse.

*Stem Cavity.*—Rounded to slightly elongated in suture plane. Average depth 7.1 mm. Average diameter 11.5 mm.

Stem:

*Size.*—Small to medium. Average length 8.0 mm. Average diameter 3.3 mm.

*Color.*—Varies from 2.5GY 6/6 to 5GY 6/8.

Flesh:

*Ripens.*—Evenly.

*Texture.*—Firm, meaty.

*Fibers.*—Few, small, tender.

*Firmness.*—Firm, comparable to other commercial varieties.

*Aroma.*—Slight, pleasant, peach aroma.

*Amydgalin.*—Undetected.

*Eating Quality.*—Good.

*Flavor.*—Good, with a good balance between acid and sugar.

*Juice.*—Slight amount.

*Acidity.*—Not available.

*Brix.*—Average Brix 13.2°, varies slightly with amount of fruit per tree and climatic conditions.

*Color.*—Varies from N 9.5/(white) to 5Y 8/2.

*Pit Cavity.*—Average length 21.3 mm. Average width 30.8 mm. Average depth 13.4mm. Color varies from 5Y 8/4 to 5R 4/12.

Skin:

*Thickness.*—Medium.

*Surface.*—Slightly waffled.

*Pubescence.*—Moderate amount, short in length.

*Tendency to Crack.*—None.

*Color.*—Ground color varies from 2.5Y 8.5/2 to 7.5Y 8/2. Overspread with 5R 6/8 to 5R 5/8.

*Tenacity.*—Tenacious to the flesh.

*Astringency.*—Slight to none.

Stone:

*Type.*—Clingstone, strong adherence to flesh.

*Size.*—Large. Average length 20.3 mm. Average width 29.8 mm. Average thickness 24.7 mm.

*Form.*—Globose.

*Base.*—Flat.

*Apex.*—Rounded.

*Surface.*—Slightly pitted throughout, pits vary from round to elongated.

*Sides.*—Unequal, one side extending further from the suture plane.

*Ridges.*—Relatively smooth, narrow ridges extending from base to apex.

*Tendency to Split.*—None.

*Color.*—Varies from 5R 3/10 to 5YR 6/4 when dry.

Kernel:

*Size.*—Small to medium. Average length 8.7 mm. Average width 12.2 mm. Average depth 7.6 mm.

*Form.*—Globose.

*Viability.*—Viable, complete embryo development.

*Skin Color.*—Varies from 5Y 9/4 to 7.5Y 9/4.

Use: Dessert. Market—local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, California, no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, California.

The invention claimed is:

1. A new and distinct variety of peach tree [(*Prunus persica*)] named 'Sauzee Treat', substantially as herein illustrated and described.

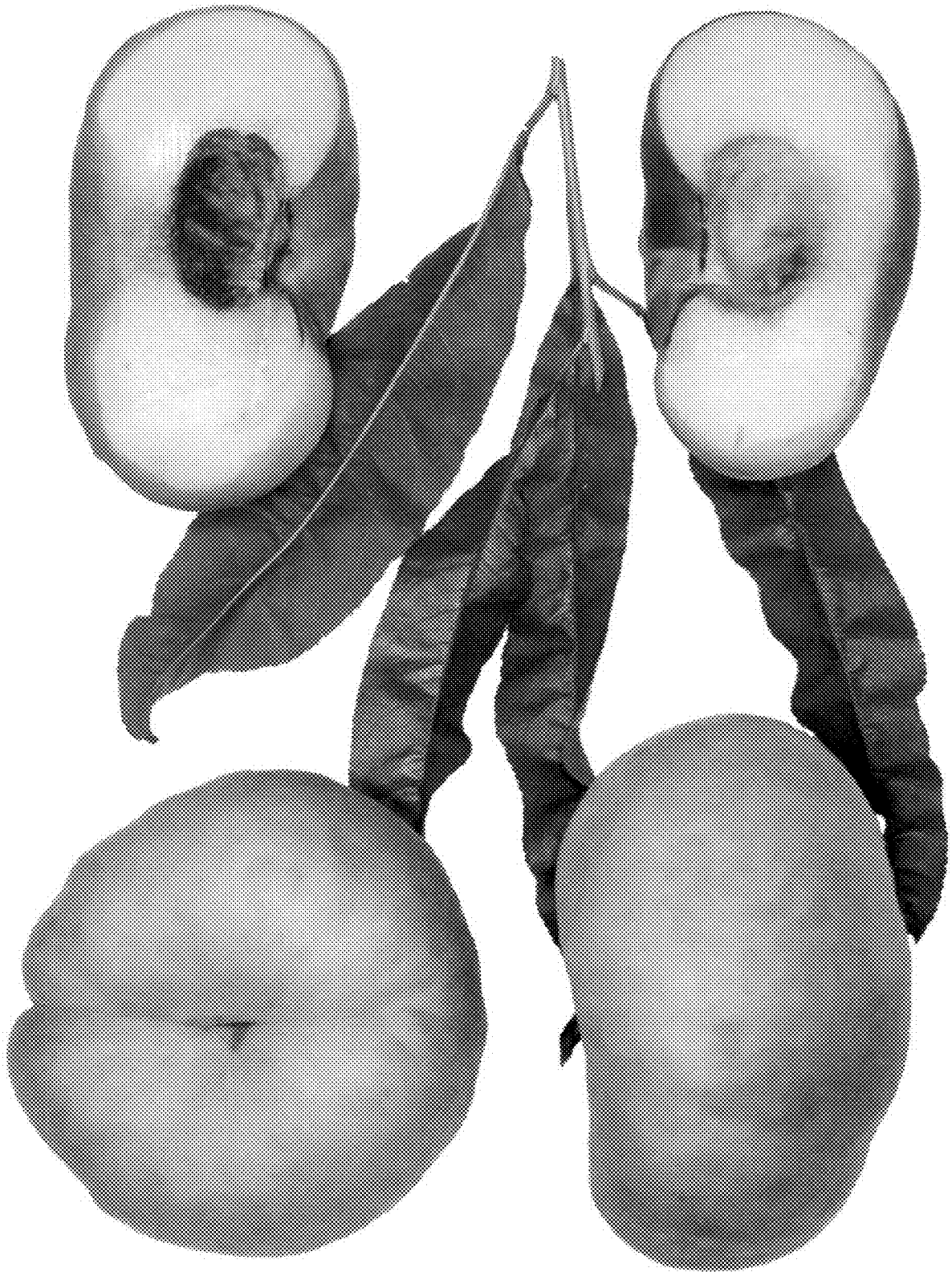

* * * * *